United States Patent
Crozier et al.

(10) Patent No.: US 11,890,050 B2
(45) Date of Patent: Feb. 6, 2024

(54) ESOPHAGEAL ABLATION TECHNOLOGY

(71) Applicant: Symple Surgical, Inc., Flagstaff, AZ (US)

(72) Inventors: Seth Crozier, Flagstaff, AZ (US); Sohail Desai, Sacramento, CA (US); Dan Kasprzyk, Flagstaff, AZ (US); Bryce Alexander Igo, Flagstaff, AZ (US)

(73) Assignee: Symple Surgical, Inc., Flagstaff, AZ (US)

( * ) Notice: Subject to any disclaimer, the term of this patent is extended or adjusted under 35 U.S.C. 154(b) by 13 days.

(21) Appl. No.: 17/556,260

(22) Filed: Dec. 20, 2021

(65) Prior Publication Data

US 2022/0125511 A1 Apr. 28, 2022

Related U.S. Application Data

(62) Division of application No. 15/486,078, filed on Apr. 12, 2017, now abandoned.

(60) Provisional application No. 62/321,239, filed on Apr. 12, 2016.

(51) Int. Cl.
*A61B 18/18* (2006.01)
*A61B 18/00* (2006.01)

(52) U.S. Cl.
CPC .. *A61B 18/1815* (2013.01); *A61B 2018/0022* (2013.01); *A61B 2018/00184* (2013.01); *A61B 2018/00196* (2013.01); *A61B 2018/00208* (2013.01); *A61B 2018/00255* (2013.01); *A61B 2018/00488* (2013.01); *A61B 2018/00577* (2013.01); *A61B 2018/00791* (2013.01); *A61B 2018/00982* (2013.01); *A61B 2018/1823* (2013.01); *A61B 2018/1861* (2013.01); *A61B 2018/1876* (2013.01)

(58) Field of Classification Search
CPC ...... A61B 18/1815; A61B 2018/00184; A61B 2018/00196; A61B 2018/00208; A61B 2018/0022; A61B 2018/00255; A61B 2018/00488; A61B 2018/00577; A61B 2018/00791; A61B 2018/00982; A61B 2018/1823; A61B 2018/1861; A61B 2018/1876
See application file for complete search history.

(56) References Cited

U.S. PATENT DOCUMENTS

| | | | |
|---|---|---|---|
| 5,057,106 A | 10/1991 | Kasevich | |
| 10,076,384 B2 | 9/2018 | Kasprzyk et al. | |
| 2011/0230798 A1 | 9/2011 | Thapliyal | |
| 2013/0178842 A1* | 7/2013 | Reid, Jr. | A61B 18/1477 606/46 |

(Continued)

*Primary Examiner* — Michael F Peffley
*Assistant Examiner* — Samantha M Good
(74) *Attorney, Agent, or Firm* — Joel Skinner; Skinner and associates

(57) ABSTRACT

An esophageal ablation system including a positioner, an elongated, flexible shaft extending from the positioner, and a microwave emitter assembly disposed near the distal end of the shaft. The emitter assembly includes one or more microwave antennae and a balloon for spacing the antennae relative to target tissue. The device may have an inner balloon for deploying the antenna. The systems, devices and methods disclosed are useful for treating Barrett's Esophagus, Esophageal Adenocarcinoma, and Squamous Cell Carcinoma.

15 Claims, 14 Drawing Sheets

(56) References Cited

U.S. PATENT DOCUMENTS

| | | |
|---|---|---|
| 2013/0281920 A1 | 10/2013 | Hawkins |
| 2014/0005660 A1 | 1/2014 | Edwards |
| 2014/0257266 A1 | 9/2014 | Kasprzyk et al. |
| 2017/0014638 A1 | 1/2017 | Preston et al. |
| 2017/0014639 A1 | 1/2017 | Preston et al. |
| 2017/0367760 A1 | 12/2017 | Crozier |
| 2019/0192224 A1 | 6/2019 | Crozier et al. |

* cited by examiner

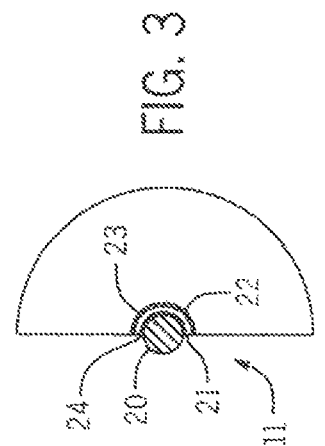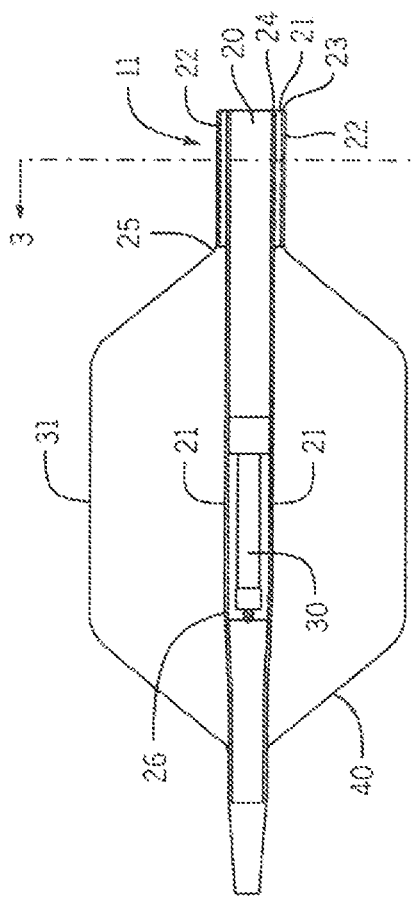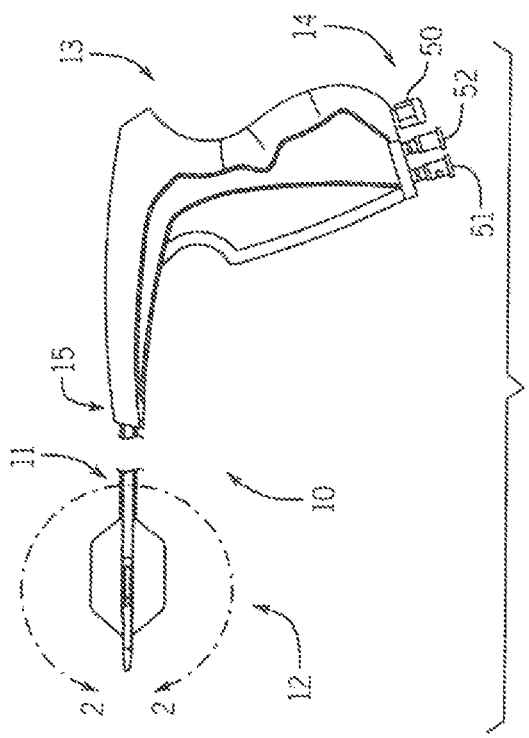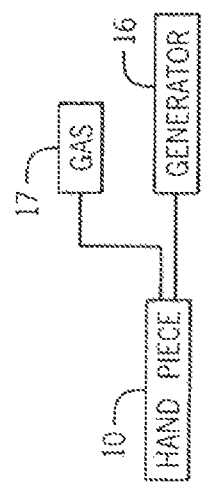

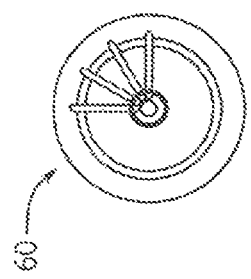
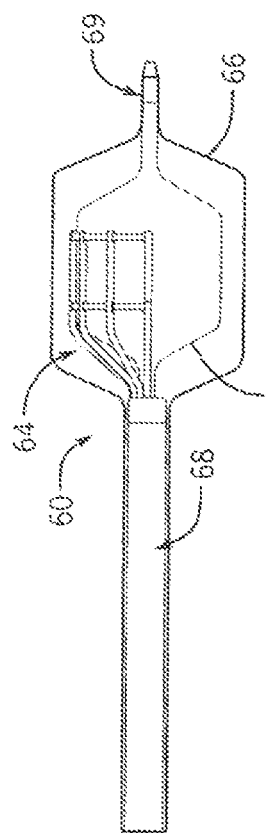
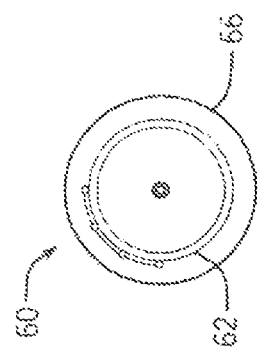
FIG. 7A  FIG. 7B  FIG. 7C
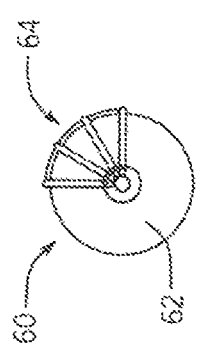
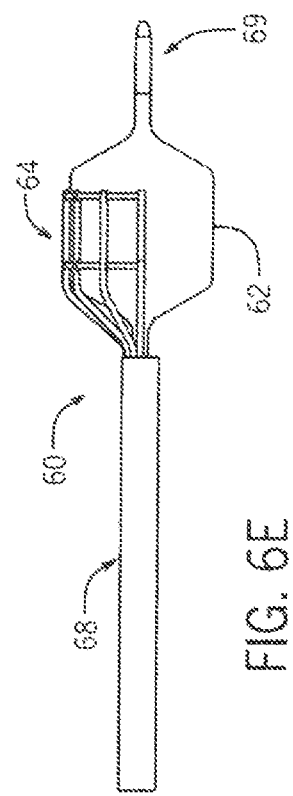
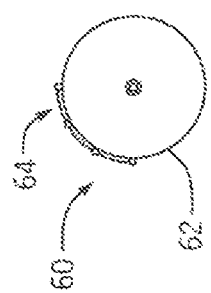
FIG. 6D  FIG. 6E  FIG. 6F
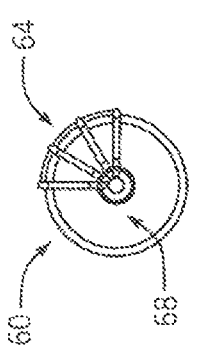
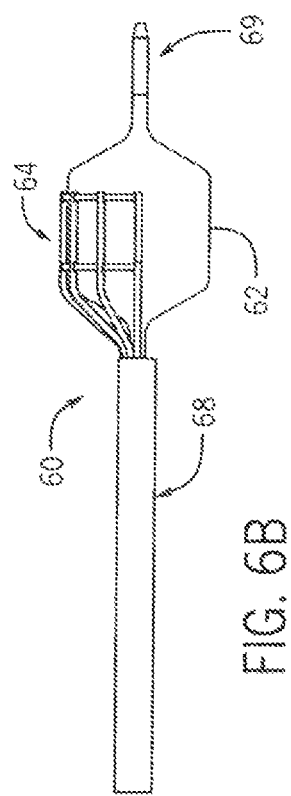
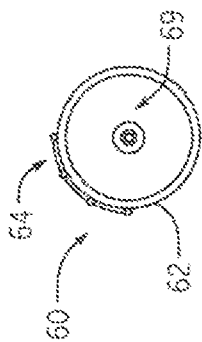
FIG. 6A  FIG. 6B  FIG. 6C

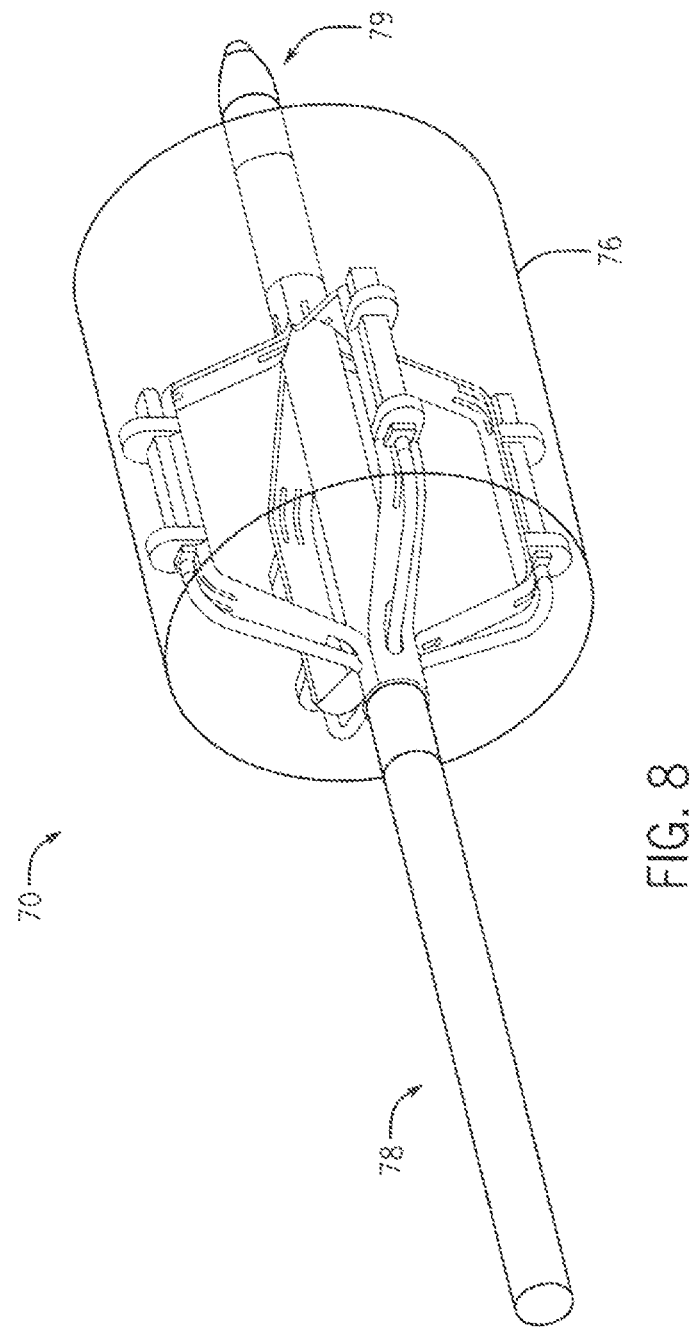

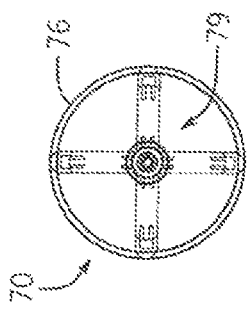
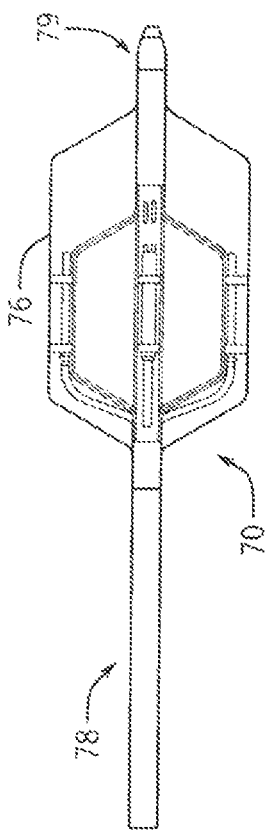
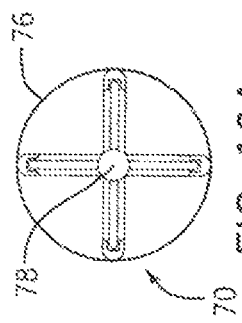
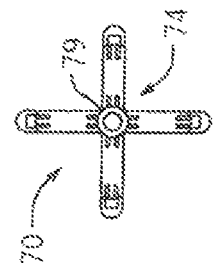
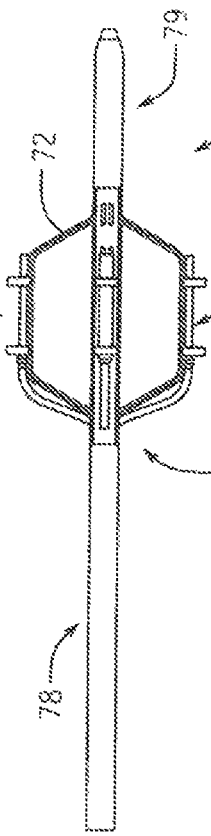
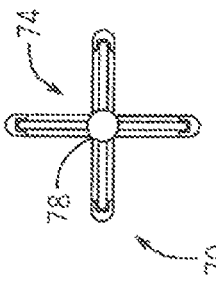
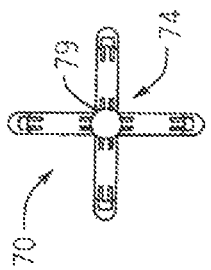
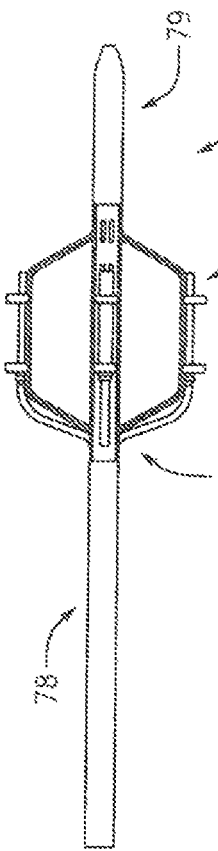
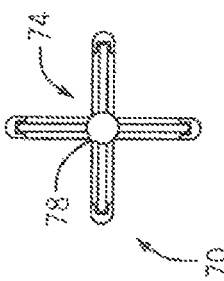

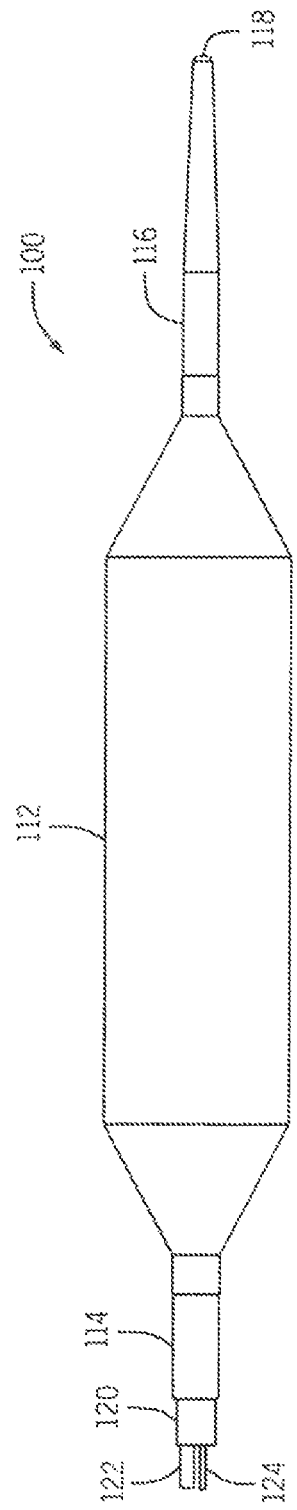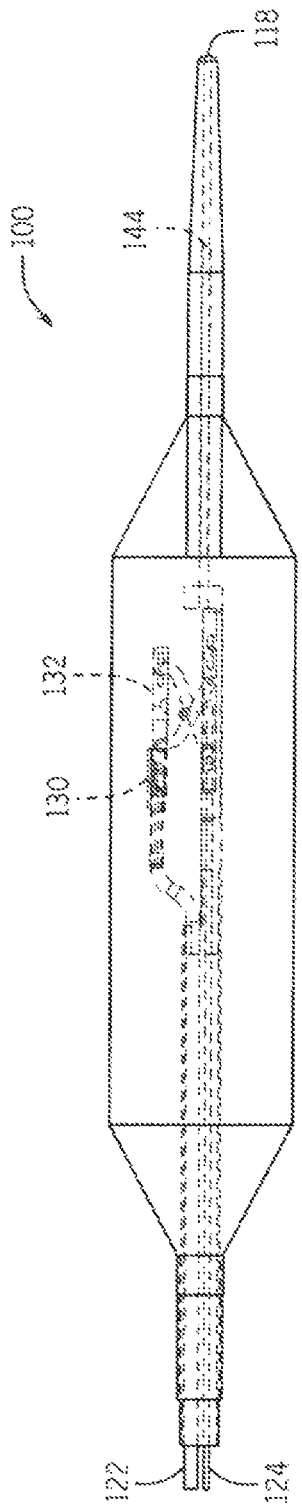

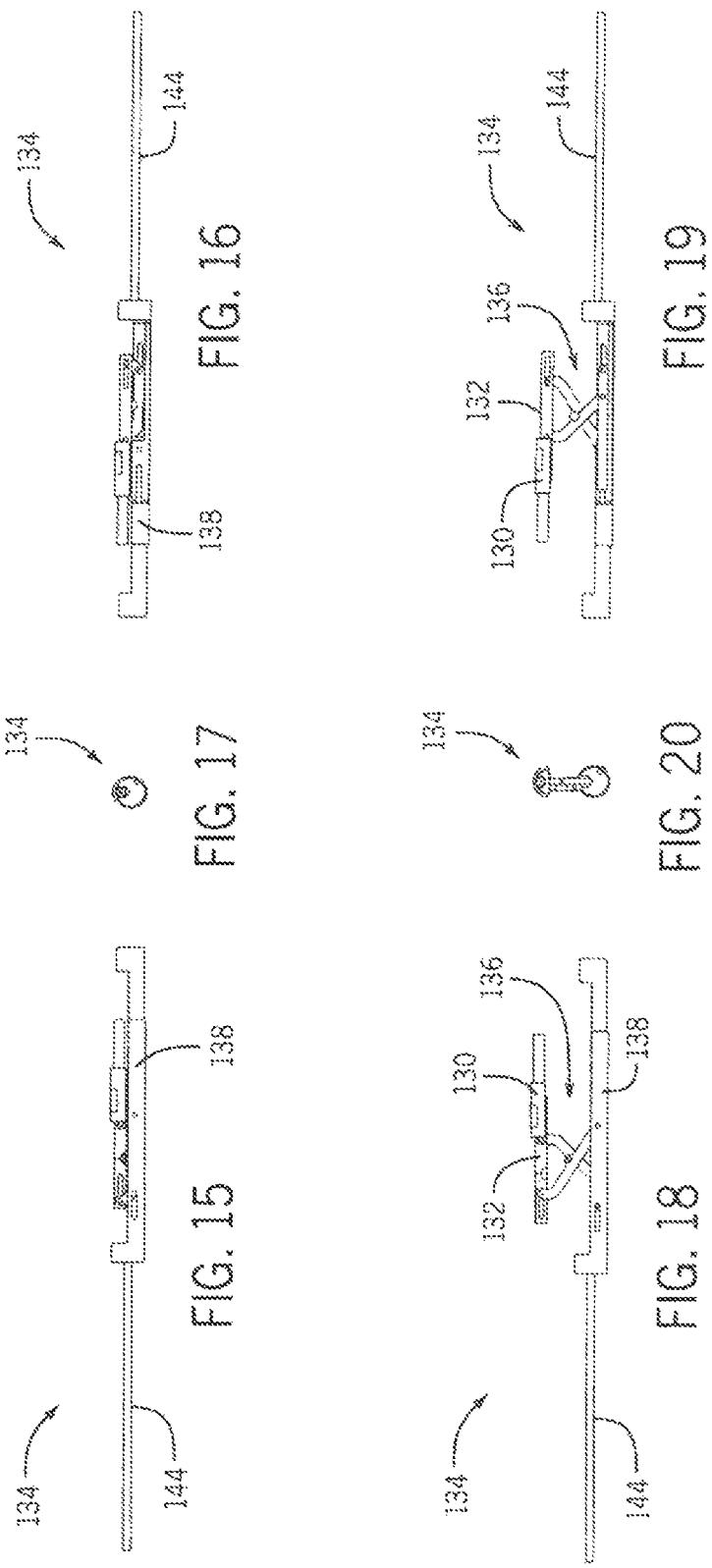

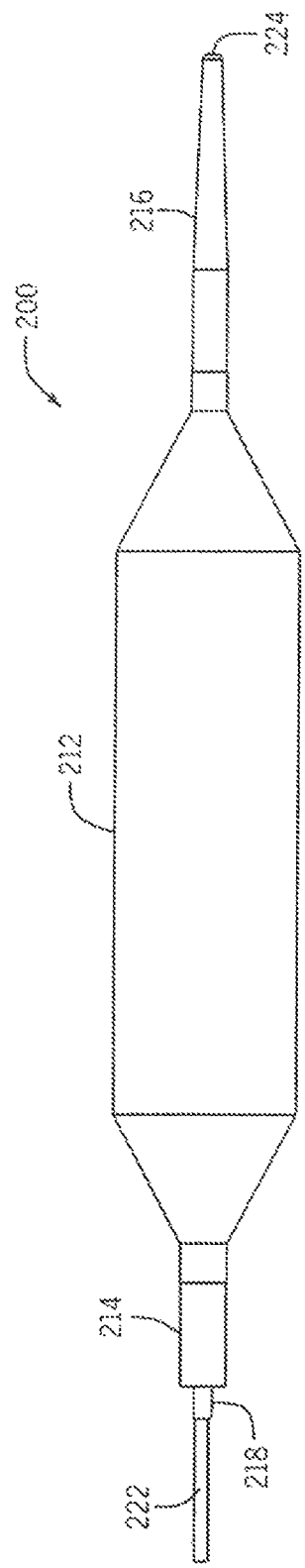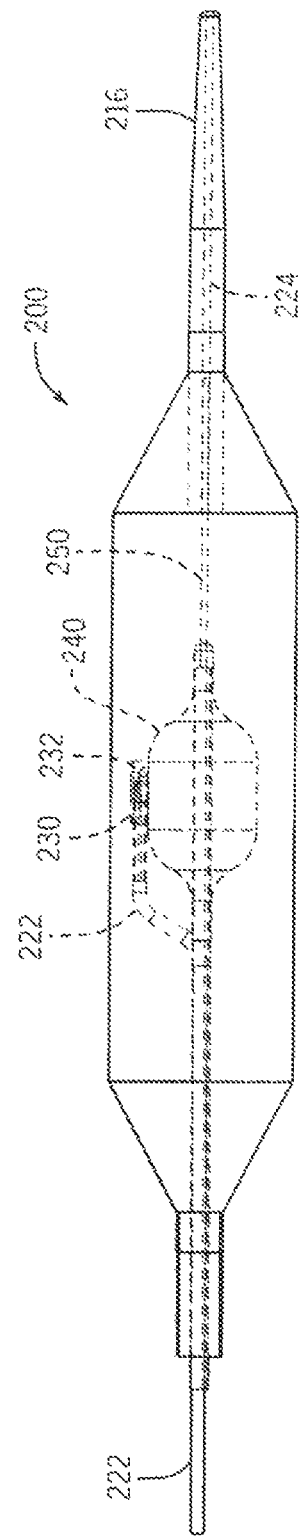
FIG. 21
FIG. 22

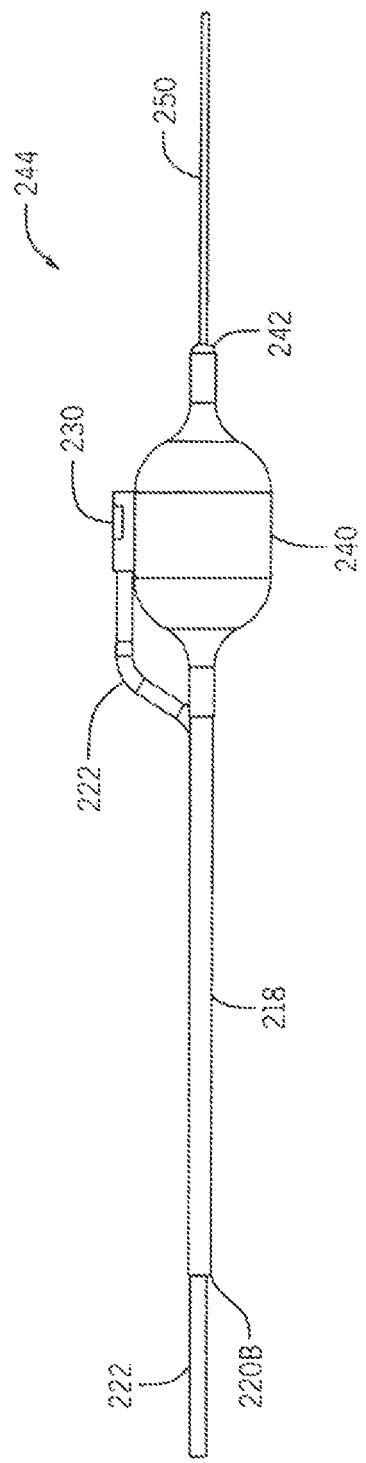

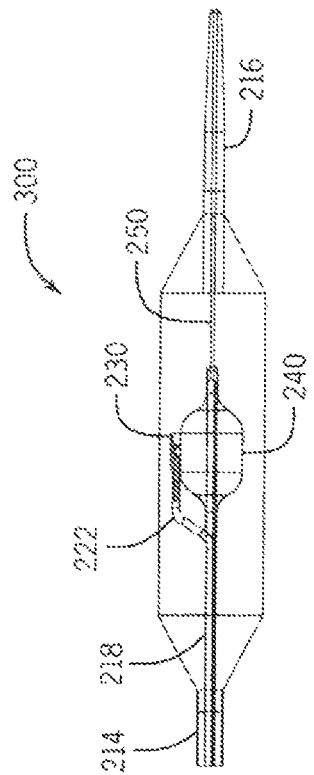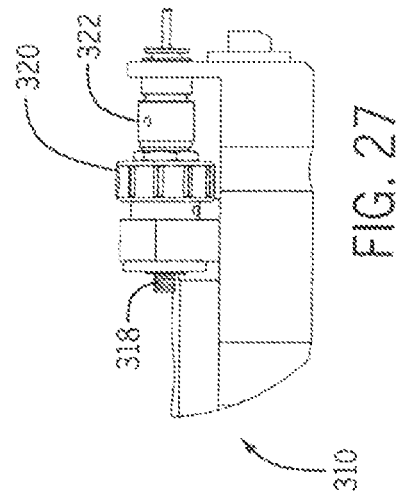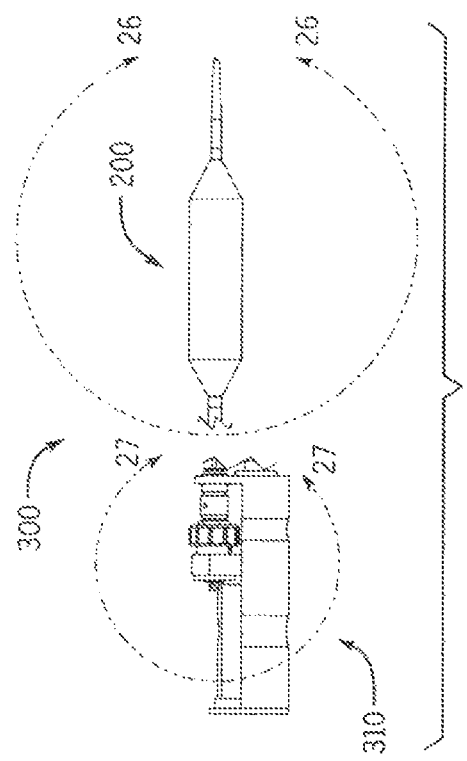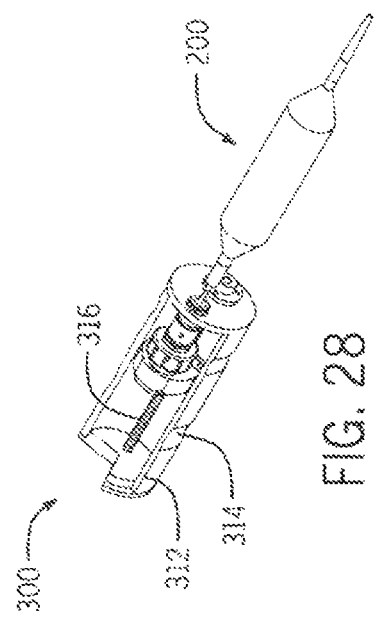

ESOPHAGEAL ABLATION TECHNOLOGY

CROSS-REFERENCE TO RELATED APPLICATIONS, IF ANY

This application is a divisional of U.S. patent application Ser. No. 15/486,078, filed Apr. 12, 2017, status abandoned, which claims the benefit under 35 U.S.C. (119(e) of U.S. Provisional Patent Application Ser. No. 62/412,2016, which is hereby incorporated by reference.

37 C.F.R. § 1.71(e) AUTHORIZATION

A portion of the disclosure of this patent document contains material which is subject to copyright protection. The copyright owner has no objection to the facsimile reproduction by anyone of the patent document or the patent disclosure, as it appears in the US Patent and Trademark Office patent file or records, but otherwise reserves all copyright rights whatsoever.

STATEMENT REGARDING FEDERALLY SPONSORED RESEARCH OR DEVELOPMENT

Not applicable.

REFERENCE TO A MICROFICHE APPENDIX, IF ANY

Not applicable.

BACKGROUND OF THE INVENTION

1. Field of the Invention

The present invention relates, generally, to thermal ablation systems, apparatus and methods. Particularly, the invention relates to a thermal ablation device and method for treating abnormal tissue in the esophagus. Most particularly, the invention relates to a device and method for use in treatments for Barrett's Esophagus, Esophageal Adenocarcinoma, Esophageal Squamous Cell Carcinoma, and the like.

2. Background Information

Barrett's esophagus is a condition in which tissue in the esophagus (a tube connecting the mouth and stomach) is replaced by tissue similar to the stomach lining. It is often diagnosed in persons who have long term gastroesophageal reflux disease (GERD). It is associated with an increased risk of developing esophageal cancer. Treatment includes management of GERD, drug therapy, and laser therapy. Treatment also includes balloon-based radio frequency ablation.

Esophageal adenocarcinoma and Esophageal squamous cell carcinoma are forms of esophageal cancer that occurs in the esophagus. Treatment typically involves chemotherapy, radiation and surgery.

Existing technology in this field is believed to have significant limitations and shortcomings. For this and other reasons, a need exists for the present invention.

US Patent Application 2012/0143180 (Lee et al.) discloses a microwave antenna housed within a balloon for treatment of Barrett's esophagus and to keep the antenna in the center of the esophagus.

2010/0168727 (Hancock et al.) discloses a balloon device for delivery of microwave radiation to the esophagus.

U.S. Pat. No. 8,442,645 (Zelickson et al.) discloses a balloon encapsulating an energy transmitting device for treatment of esophageal tissue.

U.S. Pat. No. 7,530,979 (Ganz et al.) discloses a device including a balloon member for application of microwave energy to treat Barrett's esophagus.

U.S. Pat. No. 6,846,312 (Edwards et al.) discloses a GERD treatment device having an expandable member with a microwave energy source.

U.S. Pat. No. 6,238,392 (Long) discloses a bipolar electrosurgical device for treatment of Barrett's esophagus using RF ablation and a balloon electrode.

U.S. Pat. No. 6,230,060 (Mawhinney) discloses a medical device with a balloon structure enclosing a microwave antenna.

All US patents and patent applications, and all other published documents mentioned anywhere in this application are incorporated by reference in their entirety.

BRIEF SUMMARY OF THE INVENTION

The invention provides a thermal, esophageal ablation apparatus and method which are safe and effective, and which are believed to fulfill a need and to constitute an improvement over the background technology.

In one aspect, the invention provides an microwave thermal ablation system for human medical therapy, comprising:
  a microwave generator;
  at least one microwave emitter communicatively connected to the microwave generator, the microwave emitter being adapted to being inserted into the body of a patient;
  a medical balloon inflation means; and
  a positioning balloon connected to the balloon inflation means and to the at least one microwave emitter for holding the at least one microwave emitter in a desired position relative to a target tissue or tissues within the body of a patient.

In another, narrower, aspect, the invention provides a microwave thermal ablation system for use in treating Barrett's Esophageal cells via non-contact dielectric heating, comprising:
  a. a microwave generator for providing preferably 17-18 GHz microwave energy;
  b. at least one microwave emitter communicatively connected to the microwave generator, the microwave emitter being adapted to being inserted into the body of a patient;
  c. a medical balloon inflation means;
  d. a positioning balloon connected to the balloon inflation means and to the at least one microwave emitter for holding the at least one microwave emitter in a desired position relative to a target tissue or tissues within the body of a patient, the positioning balloon being disposed around the at least one microwave emitter; and
  e. a catheter shaft including:
    (i) at least power line electrically connecting the microwave generator and the at least one microwave generator, and
    (ii) at least one lumen communicatively fluidly connecting the balloon inflation means and the positioning balloon,
the at least one microwave emitter and the positioning balloon being coupled to the catheter shaft at a predetermined position, the catheter shaft being adapted to being inserted into the body of a patient and for translating the at least one microwave emitter and the positioning balloon within and through the patient's body.

In a further aspect, the invention also provides a microwave thermal ablation method for human medical therapy, comprising the steps of:

a. providing a system including
   i. a microwave generator;
   ii. at least one microwave emitter communicatively connected to the microwave generator, the microwave emitter being adapted to being inserted into the body of a patient;
   iii. a medical balloon inflation means;
   iv. a positioning balloon connected to the balloon inflation means and to the at least one microwave emitter for holding the at least one microwave emitter in a desired position relative to a target tissue or tissues within the body of a patient; and
   v. wherein the positioning balloon is disposed on a catheter having at least one lumen for power connection between the microwave generator and the at least one microwave emitter, and fluid communication between the balloon inflation means and the positioning balloon;
b. inserting the catheter into a patient's body with the balloon in an uninflated state,
c. moving the at least one microwave emitter and surrounding positioning balloon to a desired position near target tissue that is to be thermally ablated,
d. inflating the positioning balloon to a desired diameter, thereby holding the at least one microwave emitter in a fixed position near the target tissue by the positioning balloon, and
e. delivering microwave power from the microwave generator to the at least one microwave for a predetermined period of time, at a predetermined frequency and at a predetermined phase.

The aspects, features, advantages, benefits and objects of the invention will become clear to those skilled in the art by reference to the following description, claims and drawings.

BRIEF DESCRIPTION OF THE SEVERAL VIEWS OF THE DRAWING

FIG. 1 is a perspective view of a first embodiment of the thermal ablation device of the present invention FIG. 2 is a detailed view of a distal portion of the device.

FIG. 3 is a crossectional view of a portion of the device taken along line 3-3 of FIG. 2.

FIG. 5 is a schematic of an embodiment of the handset of FIG. 1 with a microwave generator.

FIGS. 6A-C are proximal end, side elevation, and distal end views, respectively, of a second embodiment of the thermal ablation device, including a deployable antenna array with an inner deployment balloon both shown in a deployed state.

FIGS. 6D-F are proximal end, side elevation, and distal end views, respectively, of the embodiment shown in FIGS. 6A-C, with surface shading.

FIGS. 7A-C are proximal end, side elevation, and distal end views, respectively, of the embodiment of FIGS. 6A-F, including an outer positioning balloon, also deployed, and in phantom to show the relationship of internal elements.

FIG. 8 is an view, partially in phantom to reveal interior elements, of a third embodiment of the thermal ablation device.

FIGS. 9A-C are proximal end, side elevation, and distal end views, respectively, of the device of FIG. 8, with another embodiment of an antenna array and an inner deployment balloon, showed deployed.

FIGS. 9D-F are views similar to those shown in FIGS. 9A-C, with surface shading.

FIGS. 10A-C are proximal end, side elevation, and distal end views, respectively, of the embodiment of FIGS. 9A-F, including an outer positioning balloon, also deployed, and in phantom to show the relationship of layered elements.

FIG. 11 is a side elevation view of a fourth embodiment of the device of the invention, including a balloon in an expanded state.

FIG. 12 is an elevation view of the device showing certain internal components thereof in phantom in an expanded or actuated state.

FIG. 15 is a side elevation view of the scaffolding assembly and antennae of the device in a collapsed state.

FIG. 16 is an opposite side elevation view of the scaffolding assembly.

FIG. 17 is an end view of the scaffolding assembly.

FIG. 18 is a side elevation view of the scaffolding assembly and antennae of the device in an expanded state.

FIG. 19 is an opposite side elevation view of the scaffolding assembly.

FIG. 20 is an end view of the scaffolding assembly.

FIG. 21 is a side elevation view of a fifth embodiment of the device of the invention, including an external balloon in an expanded state.

FIG. 22 is an elevation view of the device showing certain internal components thereof in phantom, including an internal balloon and antennae in an expanded or actuated state

FIG. 24 is an isometric view of certain internal components of the device.

FIG. 25 is a side elevation of an embodiment of the device including the balloon assembly of FIGS. 21-24 and a handle assembly.

FIG. 26 is a detailed view of the balloon assembly, with internal components visible.

FIG. 27 is a detailed view of the handle assembly.

FIG. 28 is an isometric view of the system of FIG. 25.

DETAILED DESCRIPTION

Figure 4:
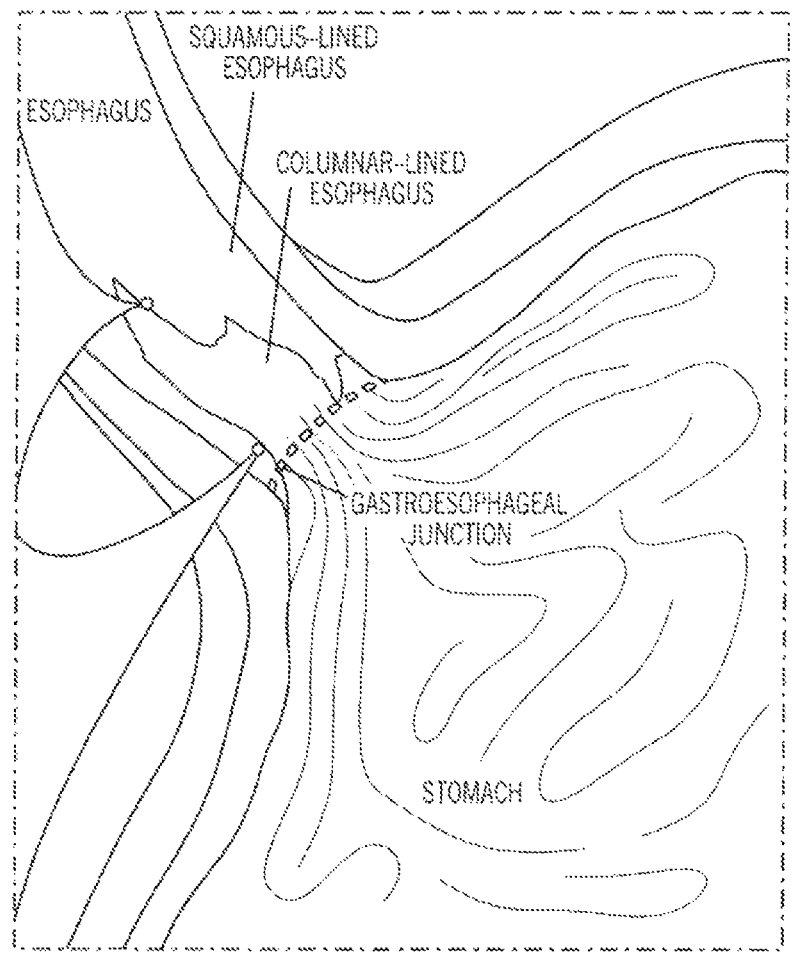
FIG. 4 is an illustration of the anatomy of a patient with Barrett's' esophagus.

The present invention provides a system, device and method for treating abnormal tissue in the esophagus. The invention is useful for treating Barrett's esophagus, esophageal adenocarcinoma, esophageal squamous cell carcinoma, and the like. The invention functions, in general, via ablation and particularly thermal ablation. The system preferably uses microwave power.

FIGS. 1-3 show a first embodiment of the esophageal ablation system of the present invention. The system 10 comprises a handset including an elongated, flexible shaft 11 and an emitter assembly 12 at the terminal, distal end of the shaft 11. The system preferably includes a hand piece type positioner 13 which is manipulated by a user to insert and steer the shaft 11 and emitter assembly 12 into and through the mouth and esophagus of a patient. The hand piece 13 has a connection end 14 for communicative mating with fluid systems and power systems. The hand piece 13 also has a distal end 15 from which the shaft 11 extends.

Referring also to FIGS. 2 and 3, the elongated, flexible shaft 11 comprises a central power cable 20, which is preferably coaxially surrounded by an inner layer 21 and an outer layer 22. The power cable 20 conducts microwave power from a power generator (shown in FIG. 5 and discussed below) to the emitter assembly 12. An outer lumen 23 is formed between the outer layer 22 and the inner layer 21, and permits inflow of fluids (air, gas, water or other liquids) used to actuate an optional balloon. An inner lumen 24 formed between the inner layer 21 and the power cable 20 permits outflow of fluids in embodiments where a balloon is used. Inflow terminates at orifice 25. Outflow initiates at orifice 26. The shaft 11 has a predetermined preferred length and outside diameter. Flow is preferably reversible.

Referring to FIG. 2, the emitter assembly 12 comprises at least one emitter antennae 30 which is communicatively connected to the distal, terminal end of the power cable 20. The emitter antennae emits microwave radiation to target tissues selected by the user clinician. The emitter 30 is preferably a broadband emitter capable of emitting a range of microwave frequencies and phases. The emitter may alternatively be a narrow-band antenna. Preferably, the antenna structurally is a coaxial antenna, patch antenna or planar antenna array. It is within the purview of the invention that the antenna may alternatively have a tri-axial, slot, helical, bow-tie, dipole or a multi-array antennae structure. The emitter may be positioned laterally, longitudinally or rotationally via the shaft 11. Additionally, the emitter may be moved in 3 dimensions during actuation. Energy may be emitted circumferentially.

During microwave emission, the antennae 30 is preferably spaced apart from the target tissue a predetermined distance. This provides non-contact dielectric heating of the tissue. The balloon 40 is preferably used for such positioning. The balloon 40 is inflated and deflated by fluid conducted to and from the inlet and outlet lumens 23 and 24. The balloon 40 may be used to position the emitter 30 centrally or off center in the esophagus relative to target tissue. The balloon 40 may be compliant, non-compliant or semi-compliant. In one embodiment, the balloon has a length of 10-60 mm, and a diameter of 14-40 mm. The balloon 40 is preferably constructed of a transparent material to permit visualization of positioning by the user via an endoscope or the like. Visualization may be made before or during emitter actuation. The device preferably has visual indicator to show target ablation zone. This could be a marking on the outer balloon such as an outline of the target ablation zone. Alternatively, it may take the form of an optical cue such as an LED/laser projection on to target ablation zone. Alternatively or additionally, the distance from the emitter 30 to the target tissue may be detected via microwave topography. The balloon's surface may include one or more shielded areas that permit or inhibit microwave transmission to control ablation. Further, the shielding may be adjustable by the user during a procedure.

In the embodiment shown the balloon 40 and emitter 30 are fixed in position relative to each other. It is within the purview of the invention that the position of the balloon 40 and emitter 30 may be varied and may be adjustable.

It is within the purview of the invention that multiple emitters may be used with the system. And although the embodiment of the system includes a balloon to position the emitter relative to the target tissue, it is also within the purview of the invention that other means of spacing may be used, including other expandable/retractable devices or assemblies. Further, the position of multiple emitters may be adjusted (rotationally, laterally and longitudinally) relative to each other. And, the emitters may be actuated independently from each other.

An alternative version of the embodiment discussed above, the hand set 10 includes a temperature sensor such as a thermocouple, thermistor, optical temperature sensor, or the like to measure tissue temperature. Alternatively, tissue properties may be measured via radiometric sensing using the emitter 30 as a receiver.

Referring to FIG. 5, the handset 10 is connectable to a microwave generator 16. The generator 16 may provides variable frequency, phase and power duty cycle to modify the thermal profile of the tissue and to control the depth of penetration of energy into the tissue. In one embodiment, the generator 16 provides a 17-18 GHz frequency range. A gas supply 17 is also connected to the handset 10. The gas supply may comprise a pump and/or a control valve connected to source of gas. Alternatively, the gas supply 17 may be integrated with the generator 16.

FIGS. 6 and 7 show a second embodiment of the device 60 of the invention with a compliant inner deployment balloon 62, an antenna array 64 mounted there over and with fixed angular spacing, and a compliant outer positioning balloon 66. The device 60 also has a proximal shaft assembly 68 and a distal tip assembly 69. The inner balloon 62 diameter may is controllable to fix or optimize the distance between the antenna 64 and the ablation target. The antenna array is rotatable from the handle to enable circumferential ablation. The antenna 64 struts constrain the arc length between adjacent antennas. This maintains the distance between antennas thereby fixing the amount of overlap between electric fields. The overlap is constant over a full diameter range.

Alternatively, the antennas may also be constructed and arranged in a linear array to cover a greater axial distance. Lastly, it is within the purview of the invention that the device 60 could be constructed of a self expanding scaffold antenna array, thereby obviating the inner balloon 62.

FIGS. 8-10 show a third embodiment of the device 70 of the invention featuring planar scaffold guides 82. The device 70 has a compliant inner deployment balloon 72, an array of four (4) antennas 74 mounted there over and with fixed angular spacing, and a compliant outer positioning balloon 76. The device 70 also has a proximal shaft assembly 78 and a distal tip assembly 79. This embodiment 70 has four antennas in a radial array. It is believed to be optimal, however, from 2 to 12 antennas may be used to practice the principles of the invention. Multiple antennas may be activated at once. Or, a single antenna may activated to ablate a narrow patch of target tissue.

This device 70 may also use a self expanding, or mechanically expandable (controlled from the handle) antenna array. However, the use of an inner balloon 72 is believed to be advantageous because the inflation fluid can be controlled and the dielectric properties of the fluid chosen for inflation modified to control ablation. A linear array may also be used to cover a greater axial surface in certain circumstances.

Referring to FIGS. 11-14, a fourth embodiment of the device 100 comprising a balloon 112 attached proximally to an outer shaft 114 and distally to a tip 116 with a thru lumen 118. The balloon 112 is preferably constructed of urethane. The balloon 112 is shown in an expanded state. It can expand to accommodate the full range of esophagi lumen diameters. The urethane balloon 112 is preferably inflated with air. The function of the urethane balloon 112 and outer shaft 114 is to create a deterministic circular lumen of known diameter inside the esophagus of a patient. The outer shaft 114 is connected to a handle and allows for the insertion of the entire assembly 110 down the mouth of the patient to the target in the esophagus. Exemplary handles embodiments are shown in FIGS. 1, 25 and 28.

Figure 13:
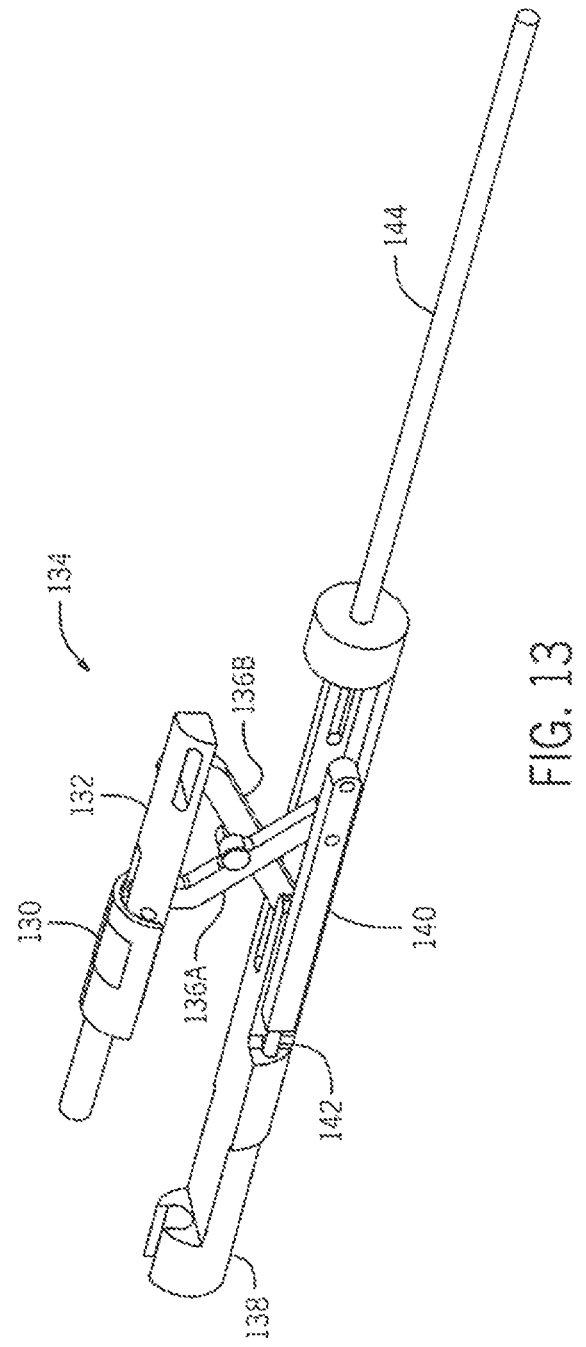
FIG. 13 is an isometric view of certain internal components of the device in an actuated state.
Figure 14:
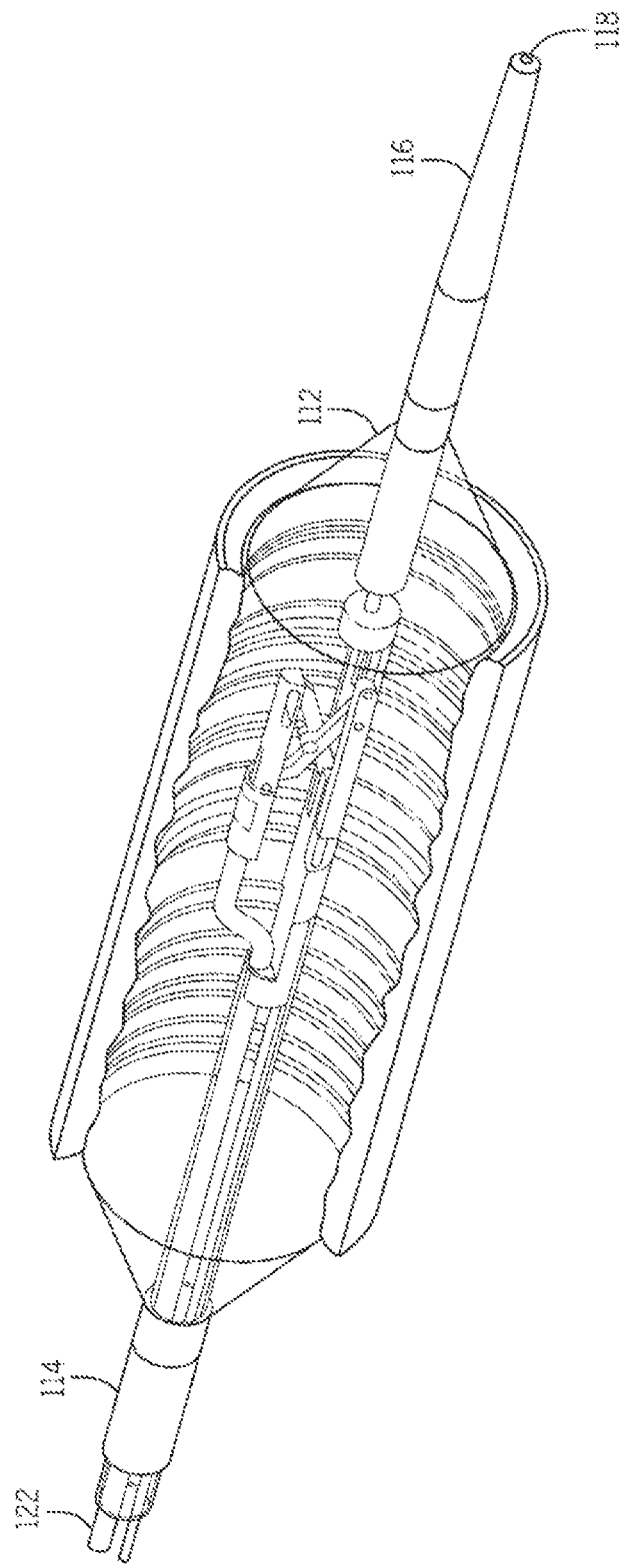
FIG. 14 is an isometric view of the device showing the device operatively disposed in the esophagus of a patient.

As is best shown in FIGS. 12-14, inside the balloon 112 and outer shaft 114 is an inner shaft 120. The inner shaft 120 contains a coaxial cable 122 and a pull wire 124. The coaxial cable 122 connects to an antenna or emitter 130. The connection is preferably a solder connection. The microwave antenna 130 is preferably a direct fed, patch type antenna that is curved around a radius. Applicants have found that curving provides mechanical advantages, and also increases the ablation zone. The antenna 130 is designed to operate preferably between 17-18 GHz. The antenna 130 and coaxial cable 122 assembly is soldered to an antenna mount 132. Referring also to FIGS. 15-20, the antenna mount 132 connects to a scaffold assembly via expansion links 136A and B. The antenna mount 132 also serves as a transition from the coaxial cable 122 to the antenna 130. This arrangement maximizes energy transfer from the cable 122 to the antenna 130 and reduces reflected power. The expansion links 136 attach to a centering/bottom link 138 and a pull link 140. The pull link 140 further connects to a pull wire 142 or mandrel. The pull wire 142 connects to a mechanism in the handle that creates the expansion and contraction of the scaffold assembly 134 and allows the user to position the antenna 130 at the correct offset from the tissue which will result in the most efficient heating of the target tissues.

The bottom/centering link 138 keeps the entire antenna assembly 130 on centerline. A telescoping shaft 144 inserts into the through lumen 118 of the outer balloon tip 116. This allows the user to rotate the antenna assembly 360° for circumferential ablations and also traverse the antenna assembly 130 longitudinally along the axis of the esophagus so that the user can perform ablations along the length of the esophagus.

It is within the purview of the invention that all mechanical movements (rotation, scaffold expansion/contraction, longitudinal movement) can be automated through the use of motors (not shown).

The most preferred frequency range of 17-18 GHz limits the depth of penetration of the ablation zone to the first 1.5 mm of tissue, which is desired for treatment of Barrett's Esophagus. Modulating input power and dwell time can further control depth of ablation.

Figure 23:
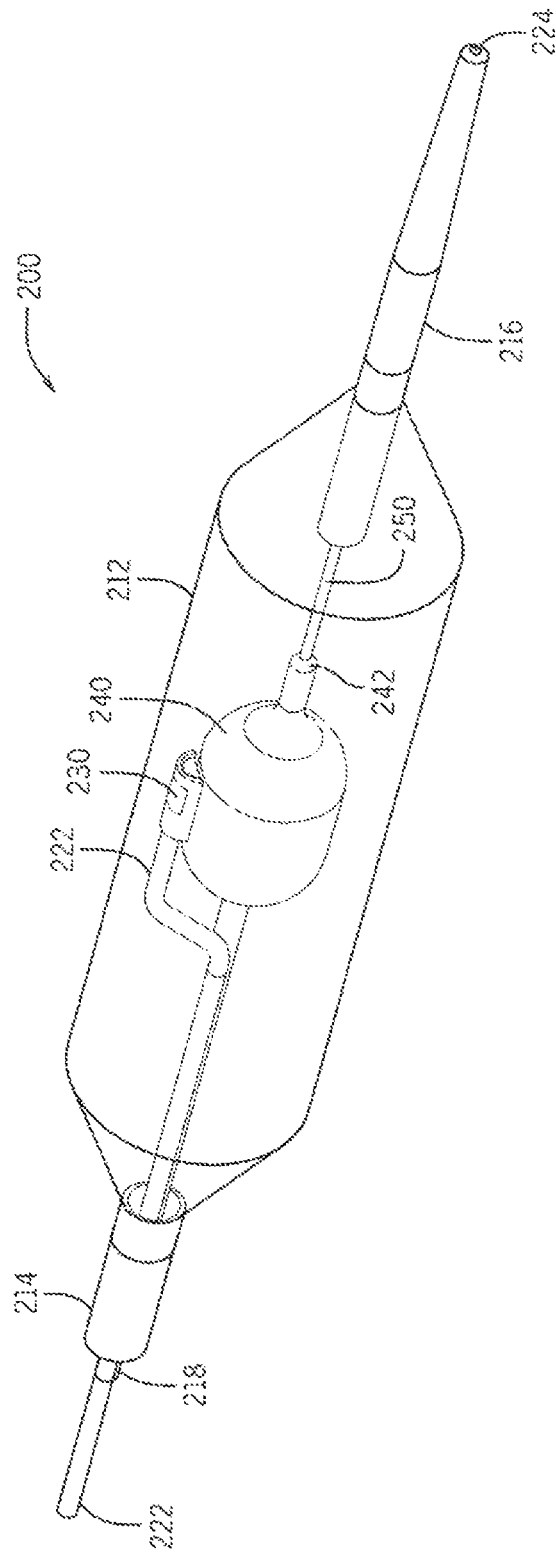
FIG. 23 is an isometric view of the device showing the device.

Referring to FIGS. 21-23, a fifth embodiment of a device 200 of the invention comprises a balloon 212 connected proximally to an outer shaft 214 and distally to a tip 218 assembly. This balloon 212 is also preferably constructed of urethane. The functions of these elements are substantially the same the same as similar structures in the previous embodiment of FIGS. 11-20.

Inside the outer balloon 212 and outer shaft 214 is an inner shaft 218, which consists of two lumens. A coaxial cable 222 extends through the first lumen. The second lumen is used to push saline through to inflate the balloon 212. The coaxial cable 222 emerges through the inner shaft 218 and attaches to an antenna 230. The antenna 230 preferably has the same structure and function as the antenna described and shown in the previous embodiment of FIGS. 11-20. The antenna 230 and coaxial cable 222 assembly once again is attached to an antenna mount 232, which serves the same purpose of efficiently transferring energy from the cable 222 to the antenna 230.

Referring also to FIG. 24, attached to the distal end of the inner shaft 218 is an inner, semi-compliant balloon 240. The inner balloon 240 is capable of multiple diametrical positions over a total diameter range increase of 1 mm-5 mm growth. The antenna mount 233 is also attached to the balloon 240. The inner balloon 240 replaces the mechanical scaffold from the previous embodiment. The balloon 240 is inflated with saline, and depending on the input pressure of the fluid, it will expand to a deterministic diameter. This permits the user to deliver the antenna 230 to the correct offset from the target tissue.

The semi-compliant balloon 240 is distally attached to the telescoping tip/shaft 250. The telescoping shaft 250 inserts into the through lumen 224 of the outer balloon tip 216. This allows the user to rotate the antenna assembly 230 360° for circumferential ablations and also traverse the antenna assembly 230 longitudinally along the axis of the esophagus so that the user can perform ablations along the length of the esophagus.

Once again, all the mechanical actions can be adapted to be fully automated. Motors can rotate and longitudinally move the inner shaft assembly. Further, an automated pump can be constructed and arranged inflate the inner, semi-compliant balloon 240 with saline to the correct diameter.

FIGS. 25-28 show an embodiment of the system 300 including the emitter assembly 200 described above with an alternative embodiment of a handle assembly 310. The handle assembly 310 includes a handle body 312 with a cavity in which is disposed a thumb wheel 320 for rotating the inner balloon 240 of the emitter 200. The thumb wheel 320 is connected at one end to an SMC push to connect rotary fitting 322. A rotating connector is disposed at the opposite end of the thumb wheel 320 for connection to an antenna power cable. A ball screw 316 provides precise longitudinal movement. The handle body 312 preferably has ergonomic grooves to facilitate optimal manual manipulation by the user.

Figure 29:
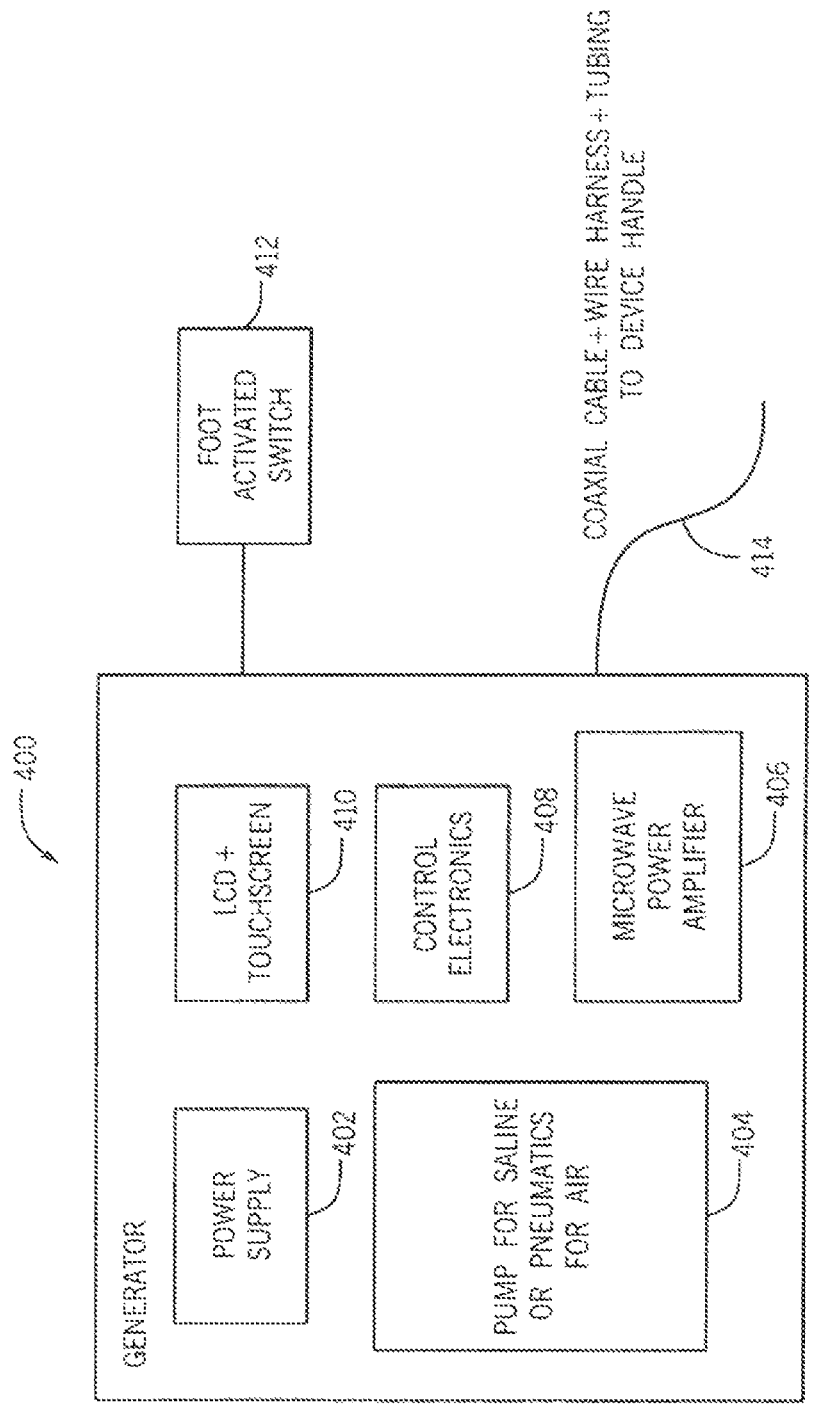
FIG. 29 illustrates an embodiment of a generator assembly usable with the system of the invention.

FIG. 29 shows an embodiment of a control assembly 400. The control assembly 400 comprises a power supply 402 communicatively connected to a controller 408 containing control electronics. A pump 404 and microwave power amplifier 406 are communicatively connected to the controller 408. The pump 404 delivers fluid (such as Saline) or gas (such as air) for hydraulic or pneumatic control of the balloons of the emitter assembly 200. The amplifier 406 powers the antenna of the emitter 200. The amplifier 406 operates in a frequency range of 915 MHz to 20 GHz. Preferred operating frequencies are 2.45 GHz, 5 GHz and 17-18 GHz. Presently, the most preferred frequency is approximately 18 GHz. Hydraulics, pneumatics and microwave power are provided via a wiring harness 414 containing applicable coaxial cable, wiring and tubing, preferably via a system handle 13 or 310 discussed above. User interface controls such as an LCD Touch Screen monitor and input 410 and/or a foot activated switch 412 are preferably communicatively connected to the controller 408.

The embodiments above are chosen, described and illustrated so that persons skilled in the art will be able to understand the invention and the manner and process of making and using it. The descriptions and the accompanying drawings should be interpreted in the illustrative and not the exhaustive or limited sense. The invention is not intended to be limited to the exact forms disclosed. While the application attempts to disclose all of the embodiments of the invention that are reasonably foreseeable, there may be unforeseeable insubstantial modifications that remain as equivalents. It should be understood by persons skilled in the art that there may be other embodiments than those disclosed which fall within the scope of the invention as defined by the claims. Where a claim, if any, is expressed as a means or step for performing a specified function it is intended that such claim be construed to cover the corresponding structure, material, or acts described in the specification and equivalents thereof, including both structural equivalents and equivalent structures, material-based equivalents and equivalent materials, and act-based equivalents and equivalent acts.

The invention claimed is:

1. A microwave thermal ablation system for human medical therapy to treat Barrett's esophagus, esophageal adenocarcinoma, and esophageal squamous cell carcinoma, comprising:
a microwave generator;
a microwave emitter communicatively connected to the microwave generator, the microwave emitter being adapted to being inserted into the esophagus of a patient, the microwave emitter including:
a centering link,
an antenna mount,
a pair of expansion links, and
an antenna,
whereby the antenna mount is adjustably connected to the centering link by the expansion links, and the antenna is connected to the antenna mount;
a medical balloon inflation means; and
a positioning balloon connected to the balloon inflation means, the positioning balloon being disposed around the at least one microwave emitter to hold the microwave emitter in a desired position relative to and spaced apart from a target tissue or tissues within the esophagus of a patient, whereby in use target esophageal cells are destroyed by non-contact dielectric heating.

2. The microwave thermal ablation system of claim 1, wherein the microwave generator provides 17-18 GHz frequency power to the microwave emitter via a power line.

3. The microwave thermal ablation system of claim 1, wherein the microwave emitter is a direct fed, patch type, antenna, with a predetermined curve.

4. The microwave thermal ablation system of claim 3 wherein the balloon inflation means is selected from the group consisting of a one way gas inflater, a reversible gas inflater, a one way liquid inflater, and a reversible liquid inflater, the balloon inflation means being connected to the positioning balloon via a fluid conduit.

5. The microwave thermal ablation system of claim 1, wherein the positioning balloon is disposed on a catheter having at least one lumen for power connection between the microwave generator and the microwave emitter, and fluid communication between the balloon inflation means and the positioning balloon.

6. The microwave thermal ablation system of claim 5, whereby, in use, (a) the catheter is inserted into a patient's esophagus with the balloon in an uninflated state, (b) the microwave emitter and surrounding positioning balloon are moved to a desired position near target esophageal tissue that is to be thermally ablated, (c) the positioning balloon is inflated to a desired diameter to create a deterministic circular lumen of a known diameter inside the esophagus of the patient, (d) the microwave emitter is held in a fixed position near, but spaced apart from, the esophageal target tissue by the positioning balloon, and (e) microwave power is delivered from the microwave generator to the microwave emitter for a predetermined period of time, at a predetermined frequency and at a predetermined phase.

7. The microwave thermal ablation system of claim 6, wherein the predetermined time, frequency, and/or phase is modulated.

8. The microwave thermal ablation system of claim 5, wherein the at least one microwave emitter is disposed in a fixed position on the catheter, whereby the at least one microwave emitter is at least generally centrally disposed within the positioning balloon.

9. The microwave thermal ablation system of claim 5, further comprising means to visually track the position of the at least one microwave emitter in the patient's esophagus during use of the system.

10. The microwave thermal ablation system of claim 9, wherein the means to visually track includes the positioning balloon being at least partially constructed of material that is transparent to users during radiographic and/or endoscopic visualization.

11. The microwave thermal ablation system of claim 1, further comprising a catheter shaft including (a) at least power line electrically connecting the microwave generator and the microwave emitter, and (b) at least one lumen communicatively fluidly connecting the balloon inflation means and the positioning balloon, the microwave emitter and the positioning balloon being coupled to the catheter shaft at a predetermined position, the catheter shaft being adapted to being inserted into the esophagus of a patient and for longitudinally translating the microwave emitter and the positioning balloon within and through the patient's esophagus.

12. The microwave thermal ablation system of claim 11, further comprising a positioning handle connected to a proximal end of the catheter shaft for inserting and steering the microwave emitter and positioning balloon into and though the mouth and esophagus of a patient, the handle being hand operable and having a distal end from which the catheter shaft extends, and a connection end for communicative mating with the balloon inflation means and the microwave generator.

13. The microwave thermal ablation system of claim 1, wherein at least a portion of the positioning balloon is constructed of material that shields microwave radiation to focus microwave radiation for directional ablation.

14. The microwave thermal ablation system of claim 1 further comprising at least one sensor selected from the group consisting of thermocouples, temperature sensors, and thermistors.

15. A microwave thermal ablation system for use in treating Barrett's Esophageal cells, esophageal adenocarcinoma, and esophageal squamous cell carcinoma via non-contact dielectric heating, comprising:
a. a microwave generator for providing 915 MHz to 20 GHz microwave energy;
b. a microwave emitter communicatively connected to the microwave generator, the microwave emitter being adapted to being inserted into the esophagus of a patient, the microwave emitter including:
a centering link,
an antenna mount,
a pair of expansion links, and
an antenna,
whereby the centering link is adjustably connected to the antenna mount by the expansion links, and the antenna is connected to the antenna mount;

c. a medical balloon inflation means;
d. a positioning balloon connected to the balloon inflation means; the positioning balloon being disposed around the microwave emitter and adapted to create a deterministic circular lumen of a known diameter inside the esophagus of a patient and to hold the microwave emitter in a desired position relative to and spaced apart from a target tissue or tissues within the esophagus of a patient, the positioning balloon being disposed around the microwave emitter, whereby, in use, target esophageal cells are destroyed by non-contact dielectric heating; and
e. a catheter shaft including:
  (i) at least one power line electrically connecting the microwave generator and the microwave emitter, and
  (ii) at least one lumen communicatively fluidly connecting the balloon inflation means and the positioning balloon, the microwave emitter and the positioning balloon being coupled to the catheter shaft at a predetermined position, the catheter shaft being adapted to being inserted into the esophagus of a patient and for translating the at least one microwave emitter and the positioning balloon within and through the patient's esophagus.

* * * * *